US012661421B2

(12) United States Patent
Perumalla et al.

(10) Patent No.: US 12,661,421 B2
(45) Date of Patent: Jun. 23, 2026

(54) DECONTAMINATION OF TRANSPORTATION VEHICLES

(71) Applicant: INTERNATIONAL BUSINESS MACHINES CORPORATION, Armonk, NY (US)

(72) Inventors: Saraswathi Sailaja Perumalla, Visakhapatnam (IN); Sarbajit K. Rakshit, Kolkata (IN); Akash U. Dhoot, Pune (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 383 days.

(21) Appl. No.: 17/817,398

(22) Filed: Aug. 4, 2022

(65) Prior Publication Data

US 2024/0042081 A1 Feb. 8, 2024

(51) Int. Cl.
A61L 2/24 (2006.01)
A61L 2/22 (2006.01)
(Continued)

(52) U.S. Cl.
CPC ................... A61L 2/24 (2013.01); A61L 2/22 (2013.01); A61L 9/015 (2013.01); (Continued)

(58) Field of Classification Search
CPC ... A61L 2/24; A61L 2/22; A61L 9/015; A61L 2202/14; A61L 2202/15; A61L 2202/16; (Continued)

(56) References Cited

U.S. PATENT DOCUMENTS

| | | |
|---|---|---|
| 10,039,848 B2 | 8/2018 | Brown |
| 2006/0289490 A1 | 12/2006 | Mielnik |

(Continued)

FOREIGN PATENT DOCUMENTS

| | | | | |
|---|---|---|---|---|
| WO | WO-2021190679 A1 * | 9/2021 | ............. | B60R 15/00 |
| WO | 2021229500 A1 | 11/2021 | | |

OTHER PUBLICATIONS

WO-2021190679 (English/OriginalTranslation) (Year: 2021).*
(Continued)

*Primary Examiner* — Sean E Conley
*Assistant Examiner* — Nebyate Seged
(74) *Attorney, Agent, or Firm* — Robert R. Aragona

(57) ABSTRACT

An embodiment for decontaminating transportation vehicles is provided. The embodiment may include receiving GPS data and real-time and historical data relating to contamination. The embodiment may also include identifying a route and location of the transportation vehicle. The embodiment may further include predicting one or more target areas to decontaminate. The embodiment may also include placing one or more decontamination devices at the target areas. The embodiment may further include identifying one or more parts of the transportation vehicle requiring decontamination. The embodiment may also include in response to determining at least one type of contamination is airborne, activating the one or more decontamination devices to increase air pressure inside the transportation vehicle and releasing the air pressure when a door is opened. The embodiment may further include deploying the one or more decontamination devices to sanitize the one or more parts of the transportation vehicle requiring decontamination.

20 Claims, 7 Drawing Sheets

300 ⌐

(51) Int. Cl.

| | |
|---|---|
| *A61L 9/015* | (2006.01) |
| *A61L 103/75* | (2026.01) |
| *B64U 80/86* | (2023.01) |
| *B64U 101/29* | (2023.01) |

(52) U.S. Cl.

CPC ....... *A61L 2103/75* (2026.01); *A61L 2202/14* (2013.01); *A61L 2202/15* (2013.01); *A61L 2202/16* (2013.01); *A61L 2209/111* (2013.01); *B64U 80/86* (2023.01); *B64U 2101/29* (2023.01)

(58) Field of Classification Search

CPC ........... A61L 2202/25; A61L 2209/111; B64U 80/86; B64U 2101/29

See application file for complete search history.

(56) References Cited

U.S. PATENT DOCUMENTS

| | | | | |
|---|---|---|---|---|
| 2018/0075417 | A1 * | 3/2018 | Gordon | B64D 1/22 |
| 2018/0186212 | A1 * | 7/2018 | Kundu | A61L 9/015 |
| 2019/0031343 | A1 * | 1/2019 | Russell | B60S 3/06 |
| 2021/0354854 | A1 * | 11/2021 | Johnson | B64D 11/00 |
| 2022/0152254 | A1 * | 5/2022 | Lee | B64D 47/02 |
| 2022/0169382 | A1 * | 6/2022 | Subramanian | A61L 2/22 |
| 2022/0185062 | A1 * | 6/2022 | Khaw | B60N 2/0021 |
| 2022/0249722 | A1 * | 8/2022 | Huitron | B08B 1/143 |

OTHER PUBLICATIONS

Disclosed Anonymously, "Auto defect and sanitize objects (equipment's, vehicles, food items etc)", IP.com, IPCOM000263146D, Aug. 2, 2020, 4 Pages.

Disclosed Anonymously, "Method and System for decontaminating a vehicle and passengers in real-time using infrared sensors", IP.com, IPCOM000257754D, Mar. 8, 2019, 3 pages. https://priorart.ip.com/IPCOM/000257754.

Disclosed Anonymously, "System and method to detect and map epidemic contaminate areas for cleaning prioritization", IP.com, IPCOM000267420D,: Oct. 26, 2021, 8 pages. https://priorart.ip.com/IPCOM/000267420.

Mell et al., "The NIST Definition of Cloud Computing", Recommendations of the National Institute of Standards and Technology, NIST Special Publication 800-145, Sep. 2011, 7 pages.

Unknown, "Decontamination of Vehicles & Equipment Used for Transportation of Potential Ebola Virus Disease (EVD) Patients or Related Equipment", Retrieved from: https://web.archive.org/web/20170521013039/https://www.hsdl.org/?view&did=758214, Retrieved on: May 21, 2017, 8 pages.

* cited by examiner

100

CLIENT COMPUTING DEVICE
102

PROCESSOR
104

DATA STORAGE
DEVICE 106

SOFTWARE
PROGRAM
108

VEHICLE
DECONTAMINATION
PROGRAM
110A

NETWORK        114

IOT DEVICE
118

SERVER 112

VEHICLE
DECONTAMINATION
PROGRAM
110B

DATABASE
116

200

DECONTAMINATION OF TRANSPORTATION VEHICLES

BACKGROUND

The present invention relates generally to the field of computing, and more particularly to a system for decontaminating transportation vehicles.

Transportation vehicles have become a common mode of delivering goods and passengers from one location to another. These transportation vehicles may include, but are not limited to, trucks, vans, and/or vehicles for hire (e.g., taxi cabs). While traveling on a roadway, the transportation vehicle may become contaminated for a variety of reasons. This contamination may impact the performance of one or more parts of the vehicle that are contaminated, and may also impact the driver of the vehicle and/or the goods (e.g., packages) that are loaded onto the transportation vehicle. For example, a contaminated package may damage or destroy the product contained inside the package.

SUMMARY

According to one embodiment, a method, computer system, and computer program product for decontaminating transportation vehicles is provided. The embodiment may include receiving GPS data and real-time and historical data relating to contamination for a transportation vehicle from one or more sources in a surrounding environment. The embodiment may also include identifying a route and a location of the transportation vehicle based on the GPS data. The embodiment may further include predicting one or more target areas of the transportation vehicle to decontaminate based on the route and the historical data. The embodiment may also include placing one or more decontamination devices at the predicted one or more target areas. The embodiment may further include identifying one or more parts of the transportation vehicle requiring decontamination based on the real-time data from the one or more sources and the location of the transportation vehicle. The embodiment may also include in response to determining at least one type of contamination is airborne, activating the one or more decontamination devices to increase air pressure inside a portion of the transportation vehicle based on a type of the transportation vehicle and releasing the air pressure inside the portion of the transportation vehicle when a door is opened. The embodiment may further include deploying the one or more decontamination devices to sanitize the one or more parts of the transportation vehicle requiring decontamination.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
FIG. 1 illustrates an exemplary networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

It is to be understood that the singular forms "a," "an," and "the" include plural referents unless the context clearly dictates otherwise. Thus, for example, reference to "a component surface" includes reference to one or more of such surfaces unless the context clearly dictates otherwise.

Embodiments of the present invention relate to the field of computing, and more particularly to a system for decontaminating transportation vehicles. The following described exemplary embodiments provide a system, method, and program product to, among other things, predict one or more target areas of a transportation vehicle to decontaminate based on a route and historical data and, accordingly, deploy one or more decontamination devices to sanitize one or more parts of the transportation vehicle. Therefore, the present embodiment has the capacity to improve transportation vehicle technology by synchronizing decontamination devices with the movement of the transportation vehicle to quickly sanitize the transportation vehicle.

As previously described, transportation vehicles have become a common mode of delivering goods and passengers from one location to another. These transportation vehicles may include, but are not limited to, trucks, vans, and/or vehicles for hire (e.g., taxi cabs). While traveling on a roadway, the transportation vehicle may become contaminated for a variety of reasons. This contamination may impact the performance of one or more parts of the vehicle that are contaminated, and may also impact the driver of the vehicle and/or the goods (e.g., packages) that are loaded onto the transportation vehicle. For example, a contaminated package may damage or destroy the product contained inside the package. If the transportation vehicle is not properly sanitized, cross contamination with other vehicles may result and/or humans loading or unloading the transportation vehicle may become sick from the contamination. This problem is typically addressed by stopping at a fixed station (e.g., a car wash) to decontaminate the transportation vehicle. However, waiting to stop at the fixed station may exacerbate the contamination and the stopping itself increases the delivery time.

It may therefore be imperative to have a system in place to properly sanitize the transportation vehicle. Thus, embodiments of the present invention may provide advantages including, but not limited to, synchronizing decontamination devices with the movement of the transportation vehicle to quickly sanitize the transportation vehicle, minimizing stops and decreasing transportation time, and proactively placing decontamination devices at strategic locations around the transportation vehicle. The present invention does not require that all advantages need to be incorporated into every embodiment of the invention.

According to at least one embodiment, when a transportation vehicle is transporting goods or passengers, GPS data and real-time and historical data relating to contamination for the transportation vehicle may be received from one or more sources in a surrounding environment in order to identify a route and a location of the transportation vehicle. Then, one or more target areas of the transportation vehicle to decontaminate may be predicted based on the route and the historical data so that one or more decontamination devices may be placed at the predicted one or more target areas. Upon placing the one or more decontamination devices, one or more parts of the transportation vehicle requiring decontamination may be identified based on the real-time data from the one or more sources and the location of the transportation vehicle. In response to determining at least one type of contamination is airborne, the one or more decontamination devices may be activated to increase air pressure inside a portion of the transportation vehicle based on a type of the transportation vehicle in order to release the air pressure inside the portion of the transportation vehicle when a door is opened. Regardless of whether the at least one type of contamination is airborne, the one or more decontamination devices may be deployed to sanitize the one or more parts of the transportation vehicle requiring decontamination. According to at least one other embodiment, in response to determining an external object is interacting with the transportation vehicle, the one or more decontamination devices may be deployed to sanitize the external object.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed concurrently or substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method, and program product to predict one or more target areas of a transportation vehicle to decontaminate based on a route and historical data and, accordingly, deploy one or more decontamination devices to sanitize one or more parts of the transportation vehicle.

Referring to FIG. 1, an exemplary networked computer environment 100 is depicted, according to at least one embodiment. The networked computer environment 100 may include client computing device 102, a server 112, and Internet of Things (IoT) Device 118 interconnected via a communication network 114. According to at least one implementation, the networked computer environment 100 may include a plurality of client computing devices 102 and servers 112, of which only one of each is shown for illustrative brevity.

The communication network 114 may include various types of communication networks, such as a wide area network (WAN), local area network (LAN), a telecommunication network, a wireless network, a public switched network and/or a satellite network. The communication network 114 may include connections, such as wire, wireless communication links, or fiber optic cables. It may be appreciated that FIG. 1 provides only an illustration of one implementation and does not imply any limitations with regard to the environments in which different embodiments may be implemented. Many modifications to the depicted environments may be made based on design and implementation requirements.

Client computing device 102 may include a processor 104 and a data storage device 106 that is enabled to host and run a software program 108 and a vehicle decontamination program 110A and communicate with the server 112 and IoT Device 118 via the communication network 114, in accordance with one embodiment of the invention. Client computing device 102 may be, for example, a mobile device, a telephone, a personal digital assistant, a netbook, a laptop computer, a tablet computer, a desktop computer, or any type of computing device capable of running a program and accessing a network. As will be discussed with reference to FIG. 4, the client computing device 102 may include internal components 402a and external components 404a, respectively.

The server computer 112 may be a laptop computer, netbook computer, personal computer (PC), a desktop computer, or any programmable electronic device or any network of programmable electronic devices capable of hosting and running a vehicle decontamination program 110B and a database 116 and communicating with the client computing device 102 and IoT Device 118 via the communication network 114, in accordance with embodiments of the invention. As will be discussed with reference to FIG. 4, the server computer 112 may include internal components 402b and external components 404b, respectively. The server 112 may also operate in a cloud computing service model, such as Software as a Service (SaaS), Platform as a Service (PaaS), or Infrastructure as a Service (IaaS). The server 112 may also be located in a cloud computing deployment model, such as a private cloud, community cloud, public cloud, or hybrid cloud.

IoT Device 118 may be a transportation vehicle (e.g., a truck, van, and/or vehicle for hire), a GPS-enabled device internal or external to the transportation vehicle, a thermal camera, odor detection sensors, a robotic device, and/or any IoT Device 118 known in the art for detecting performance of vehicle parts that is capable of connecting to the communication network 114, and transmitting and receiving data with the client computing device 102 and the server 112.

According to the present embodiment, the vehicle decontamination program 110A, 110B may be a program capable of receiving GPS data and real-time and historical data relating to contamination for a transportation vehicle from one or more sources in a surrounding environment, predicting one or more target areas of the transportation vehicle to decontaminate based on a route of the transportation vehicle and the historical data, deploying one or more decontamination devices to sanitize one or more parts of the transportation vehicle, synchronizing the decontamination devices with the movement of the transportation vehicle to quickly sanitize the transportation vehicle, minimizing stops and decreasing transportation time, and proactively placing the decontamination devices at strategic locations around the transportation vehicle. The vehicle decontamination method is explained in further detail below with respect to FIGS. 2A and 2B.

Figure 2A:
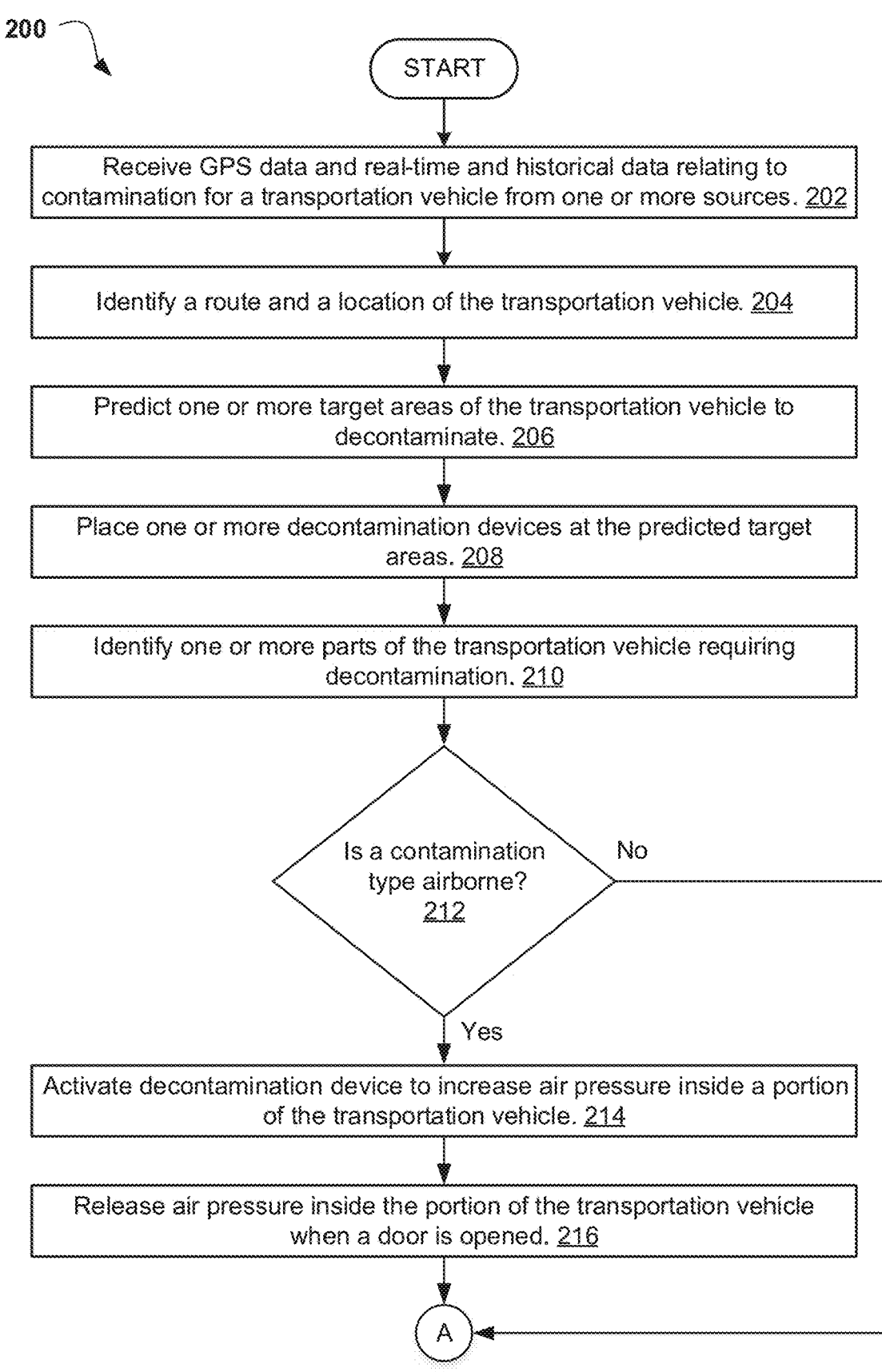
FIGS. 2A and 2B illustrate an operational flowchart for decontaminating transportation vehicles in a vehicle decontamination process according to at least one embodiment.
Figure 2B:
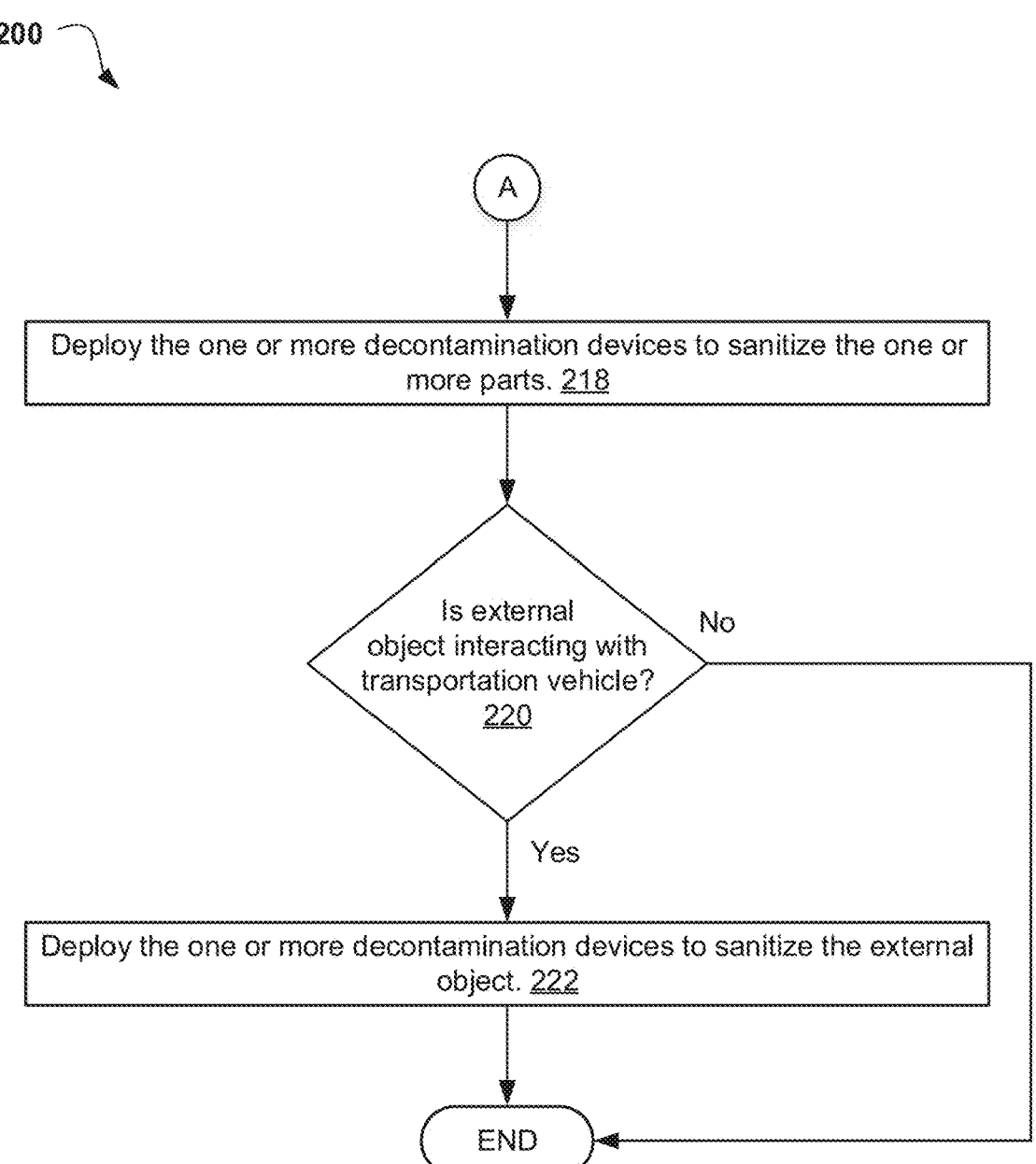

Referring now to FIGS. 2A and 2B, an operational flowchart for decontaminating transportation vehicles in a vehicle decontamination process 200 is depicted according to at least one embodiment. At 202, the vehicle decontamination program 110A, 110B receives the GPS data and the real-time and historical data relating to contamination for a transportation vehicle from one or more sources in a surrounding environment. The transportation vehicle may include, but is not limited to, a truck, van, and/or vehicle for hire (e.g., taxi cab). The one or more sources may include, but are not limited to, a plurality of odor detection sensors, a GPS device, a database containing information about air quality in a geographical area, a thermal camera, and/or other sensors detecting performance of vehicle parts (e.g., engine temperature sensors).

The GPS data may include, but is not limited to, information such as a map of the surrounding environment (e.g., a city, town, or rural area), a route of the transportation vehicle, a location of the transportation vehicle, a speed of the transportation vehicle, and/or a vehicle type of the transportation vehicle (e.g., a truck or taxi cab). The GPS data may be received by the vehicle decontamination program 110A, 110B when the transportation vehicle is actively navigating to a programmed destination.

The real-time data may include, but is not limited to, information such as odors at the location of the transportation vehicle, performance of vehicle parts, and/or external objects interacting with the transportation vehicle. The historical data may include, but is not limited to, information such as air quality in a given geographical area and/or target areas of the transportation vehicle which typically get contaminated along the route. The target areas of the transportation vehicle are described in further detail below with respect to step 206.

Then, at 204, the vehicle decontamination program 110A, 110B identifies the route and the location of the transportation vehicle. The route and the location are identified based on the GPS data. As described above with respect to step 202, the GPS data may include the route and the location of the transportation vehicle. For example, while navigating to a destination, the route may include the transportation vehicle taking "Highway A," Highway B", and "Highway D," and a current location of the transportation vehicle may be at mile marker 25 on "Highway A."

Next, at 206, the vehicle decontamination program 110A, 110B predicts the one or more target areas of the transportation vehicle to decontaminate. The one or more target areas to decontaminate are predicted based on the route and the historical data. As described above with respect to step 202, the historical data may include target areas of the transportation vehicle which typically get contaminated along the route. The one or more target areas may be one or more parts of the transportation vehicle which typically get contaminated along the route. For example, if the wheels of the transportation vehicle typically get contaminated while traveling along "Highway B" in the past, then when a current route of the transportation vehicle includes "Highway B," the wheels may be predicted to be a target area. Thus, the one or more target areas may be the one or more parts of the transportation vehicle that are most likely to become contaminated along the current route based on prior instances of contamination. Examples of contamination may include, but are not limited to, dirt or dust accumulation on the one or more parts of the transportation vehicle, an airborne bacteria or germ accumulation, and/or any other foreign substances (e.g., liquids) that accumulate on the one or more parts. The predicted one or more target areas may be utilized to strategically and proactively arrange the one or more decontamination devices on the transportation vehicle, described in further detail below with respect to step 208. It may be appreciated that the examples described above are not intended to be limiting, and that in embodiments of the present invention different parts of the transportation vehicle may become contaminated along different routes.

Figure 3:
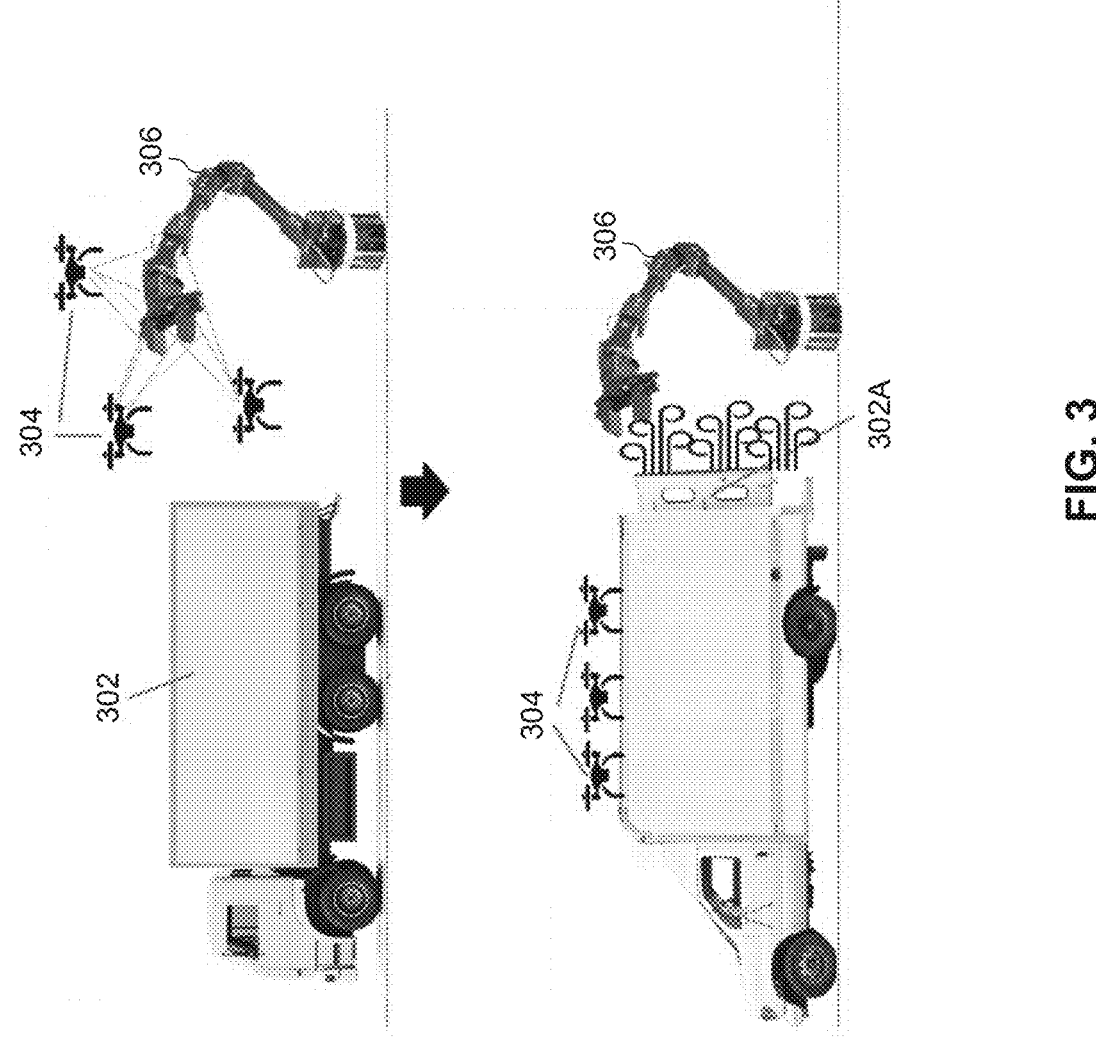
FIG. 3 is a diagram depicting an operational example of a decontamination device decontaminating a robotic device and a preventive action taken by the transportation vehicle according to at least one embodiment.

Then, at 208, the vehicle decontamination program 110A, 110B places the one or more decontamination devices at the predicted one or more target areas described above with respect to step 206. Examples of the decontamination device include, but are not limited to, a drone, a robotic device, and/or a blower (e.g., a high-powered fan). The one or more decontamination devices may be detachable decontamination devices. Thus, the one or more decontamination devices may include mobile decontamination devices capable of moving from one location to another to perform the decontamination, as illustrated in FIG. 3 and described in further detail below with respect to steps 218 and 222. Continuing the example above where the wheels of the transportation vehicle typically get contaminated while traveling along "Highway B," then when a current route of the transportation vehicle includes "Highway B," at least one decontamination device may be initially placed at the wheels. In another example, when the roof of the transportation vehicle typically gets contaminated while traveling along "Highway B," at least one decontamination device may be initially placed on the roof, as illustrated in FIG. 3.

According to at least one embodiment, the vehicle decontamination program 110A, 110B may place the one or more decontamination devices at the predicted one or more target areas automatically by sending a signal to the one or more decontamination devices to move to the target areas. In this embodiment, the one or more decontamination devices are capable of flying from one location to another. According to at least one other embodiment, a user, such as a human, may manually place the one or more decontamination devices at the predicted one or more target areas. In this embodiment, the vehicle decontamination program 110A, 110B may send the user a notification regarding the location of the one or more target areas.

Next, at 210, the vehicle decontamination program 110A, 110B identifies the one or more parts of the transportation vehicle requiring decontamination. The one or more parts are identified based on the real-time data from the one or more sources and the location of the transportation vehicle. The one or more parts requiring decontamination may either be the same as or different from the predicted one or more target areas. As described above with respect to step 202, the real-time data may include odors at the location of the transportation vehicle as well as performance of vehicle parts, and the source may include odor detection sensors and/or other sensors detecting performance of vehicle parts (e.g., engine temperature sensors). The IoT Device 118 feed from these sensors may indicate which parts of the transportation vehicle have become contaminated.

For example, the IoT Device 118 feed may include a certain reading during the normal operation of the one or more parts, and another reading when the one or more parts have become contaminated. Additionally, due to contamination, a sensor associated with a part may not be transmitting any data. Thus, when any reading for a part deviates from the normal reading or there is no reading at all, that part may be contaminated. Continuing the example, when the normal tire pressure for the wheels of the transportation vehicle is 30 pounds per square inch (psi), and the tire pressure drops to 20 psi when the transportation vehicle is traveling on "Highway C," the vehicle decontamination program 110A, 110B may identify the wheel and/or tire is contaminated. The location of the transportation vehicle may supplement the real-time data. Since the historical data includes air quality in a given geographical area, the location of the transportation vehicle may indicate the one or more parts requiring decontamination. For example, when the transportation vehicle passes mile marker 17 on "Highway C," and at mile marker 17 there is a known germ that contaminates the paint on the hood of the transportation vehicle, then even without the real-time data the vehicle decontamination program 110A, 110B may identify that the hood is contaminated. It may be appreciated that the examples described above are not intended to be limiting, and that in embodiments of the present invention the air quality at any location may vary.

Then, at 212, the vehicle decontamination program 110A, 110B determines whether at least one type of contamination is airborne. Examples of an airborne contamination type include, but are not limited to, a foul odor, a toxic gas, and/or a bacterial germ. According to at least one embodiment, the determination may be made based on the real-time data from the one or more sources. For example, the odor sensors may detect the foul odor at the location of the transportation vehicle. According to at least one other embodiment, the determination may be made based on the route of the transportation vehicle and the historical data about the air quality along that route. For example, the historical data about the air quality may indicate the presence of a toxic gas due to a factory located on the route. It may be appreciated that the examples described above are not intended to be limiting, and that in embodiments of the present invention a variety of other factors may cause the airborne contamination.

In response to determining the at least one contamination type is airborne (step 212, "Yes" branch), the vehicle decontamination process 200 proceeds to step 214 to activate the one or more decontamination devices to increase the air pressure inside the portion of the transportation vehicle based on the type of the transportation vehicle. In response to determining the at least one contamination type is not airborne (step 212, "No" branch), the vehicle decontamination process 200 proceeds directly to step 218 to deploy the one or more decontamination devices to sanitize the one or more parts of the transportation vehicle requiring decontamination.

Next, at 214, the vehicle decontamination program 110A, 110B activates the one or more decontamination devices to increase the air pressure inside the portion of the transportation vehicle based on the type of the transportation vehicle. In this embodiment, the one or more decontamination devices may include a plurality of blowers (e.g., high-powered fans) and/or any device known in the art to increase air pressure inside a vehicle. The vehicle decontamination program 110A, 110B may activate the one or more decontamination devices by sending a signal to the one or more decontamination devices to increase the air pressure in the appropriate portion of the transportation vehicle.

The portion of the transportation vehicle in which to activate the one or more decontamination devices may be identified based on the type of the transportation vehicle. For example, if the transportation vehicle is a truck or van carrying packages or other cargo, the air pressure may be increased in the container to prevent the airborne contamination from reaching the packages or cargo. In another example, if the transportation vehicle is a for hire vehicle (e.g., a taxi cab), then the air pressure may be increased in the passenger cabin rather than in the trunk or engine compartment.

Then, at 216, the vehicle decontamination program 110A, 110B releases the air pressure inside the portion of the transportation vehicle when a door is opened. The air pressure may be released by the one more activated decontamination devices blowing air out of the portion of the transportation vehicle when the door is opened, as illustrated in FIG. 3. In embodiments where the transportation vehicle is the truck or van, the door that is opened may be a door to a container of the transportation vehicle, as illustrated in FIG. 3. In embodiments where the transportation vehicle is the for hire vehicle, the door that is opened may be a door to the passenger compartment. By blowing the air out of the portion of the transportation vehicle, the airborne contamination may be prevented from entering the transportation vehicle.

Next, at 218, the vehicle decontamination program 110A, 110B deploys the one or more decontamination devices to sanitize the one or more parts of the transportation vehicle requiring decontamination. In this embodiment, the one or more decontamination devices may include a plurality of drones. As described above with respect to step 208, the one or more decontamination devices may be proactively placed at the predicted one or more target areas. According to at least one embodiment, the predicted one or more target areas may be the same as the one or more parts requiring decontamination. In this embodiment, the one or more decontamination devices may detach from the predicted one or more target areas and hover above or adjacent to the one or more parts requiring decontamination to sanitize the one or more parts. According to at least one other embodiment, the one or more parts requiring decontamination may be different than the predicted one or more target areas. In this embodiment, the one or more decontamination devices may detach from the predicted one or more target areas and fly to the one or more parts requiring decontamination. For example, when the one or more decontamination devices are initially placed at the wheel of the transportation vehicle, but during travel the door becomes contaminated, the one or more decontamination devices may detach from the wheel, and fly to the door to sanitize the door.

In either embodiment, the one or more decontamination devices may sanitize the one or more parts by methods including, but not limited to, spraying a chemical cleaning agent on the one or more parts, through ultrasound, and/or via infrared radiation. The particular type of method used may be based on the type of contamination. For example, when dirt or dust accumulates on the wheel, the one or more decontamination devices may spray the chemical cleaning agent on the wheel. It may be appreciated that the examples described above are not intended to be limiting, and that in embodiments of the present invention different sanitizing methods may be used for different types of contamination.

According to at least one further embodiment, the transportation vehicle may be in motion while the one or more decontamination devices are deployed to sanitize the one or more parts. When the transportation vehicle is in motion, the one or more decontamination devices, such as the plurality of drones, may detach from a surface of the transportation vehicle and may synchronously move relative to the transportation vehicle to sanitize the one or more parts. For example, the detached plurality of drones may sanitize the one or more parts by spraying a chemical on the one or more parts while the transportation vehicle is in motion.

Then, at 220, the vehicle decontamination program 110A, 110B determines whether the external object is interacting with the transportation vehicle. The external object may be a robotic device. For example, the robotic device may be tasked with loading and unloading packages or other cargo from the transportation vehicle, as illustrated in FIG. 3. The determination may be made by a thermal camera detecting the external object touching the transportation vehicle and/or walking toward the transportation vehicle. For example, the external object may be touching the transportation vehicle to open the door to a container of the transportation vehicle.

In response to determining the external object is interacting with the transportation vehicle (step 220, "Yes" branch), the vehicle decontamination process 200 proceeds to step 222 to deploy the one or more decontamination devices to sanitize the external object. In response to determining the external object is not interacting with the transportation vehicle (step 220, "No" branch), the vehicle decontamination process 200 ends.

Next, at 222, the vehicle decontamination program 110A, 110B deploys the one or more decontamination devices to sanitize the external object. The one or more decontamination devices may detach from a surface of the transportation vehicle and fly to the external object to sanitize the external object, as illustrated in FIG. 3. The one or more decontamination devices may hover above or adjacent to the external object and may sanitize the external object by any of the methods described above with respect to step 218. In this manner, germs on the external object may not be transferred to the packages or other cargo in the transportation vehicle. The external object may be prevented from entering an interior of the transportation vehicle while the deployed one or more decontamination devices sanitize the external object. For example, the door of the transportation vehicle may remain locked until the one or more decontamination devices are finished sanitizing the external object.

Referring now to FIG. 3, a diagram 300 depicting an operational example of a decontamination device 304 decontaminating a robotic device 306 and a preventive action taken by the transportation vehicle 302 is shown according to at least one embodiment. In the diagram 300, the transportation vehicle 302 may be a truck carrying packages or other cargo from one location to another. According to at least one embodiment, the one or more decontamination devices 304 may detach from a surface of the transportation vehicle 302 and hover over and/or adjacent to the robotic device 306 to sanitize the robotic device 306. For example, the one or more decontamination devices 304 may sanitize the robotic device 306 by spraying a chemical cleaning agent on the robotic device 306.

According to at least one other embodiment, upon finishing the sanitization of the robotic device 306, the one or more decontamination devices 304 may move back to the transportation vehicle 302. When there is the airborne contamination at the location of the transportation vehicle 302, a plurality of blowers (not shown) may increase the air pressure in the container of the transportation vehicle 302. When a door 302A to the container of the transportation vehicle 302 is opened, the air may flow out of the container such that the packages or other cargo are not affected by the airborne contamination.

It may be appreciated that FIGS. 2A, 2B, and 3 provide only an illustration of one implementation and do not imply any limitations with regard to how different embodiments may be implemented. Many modifications to the depicted environments may be made based on design and implementation requirements.

Figure 4:
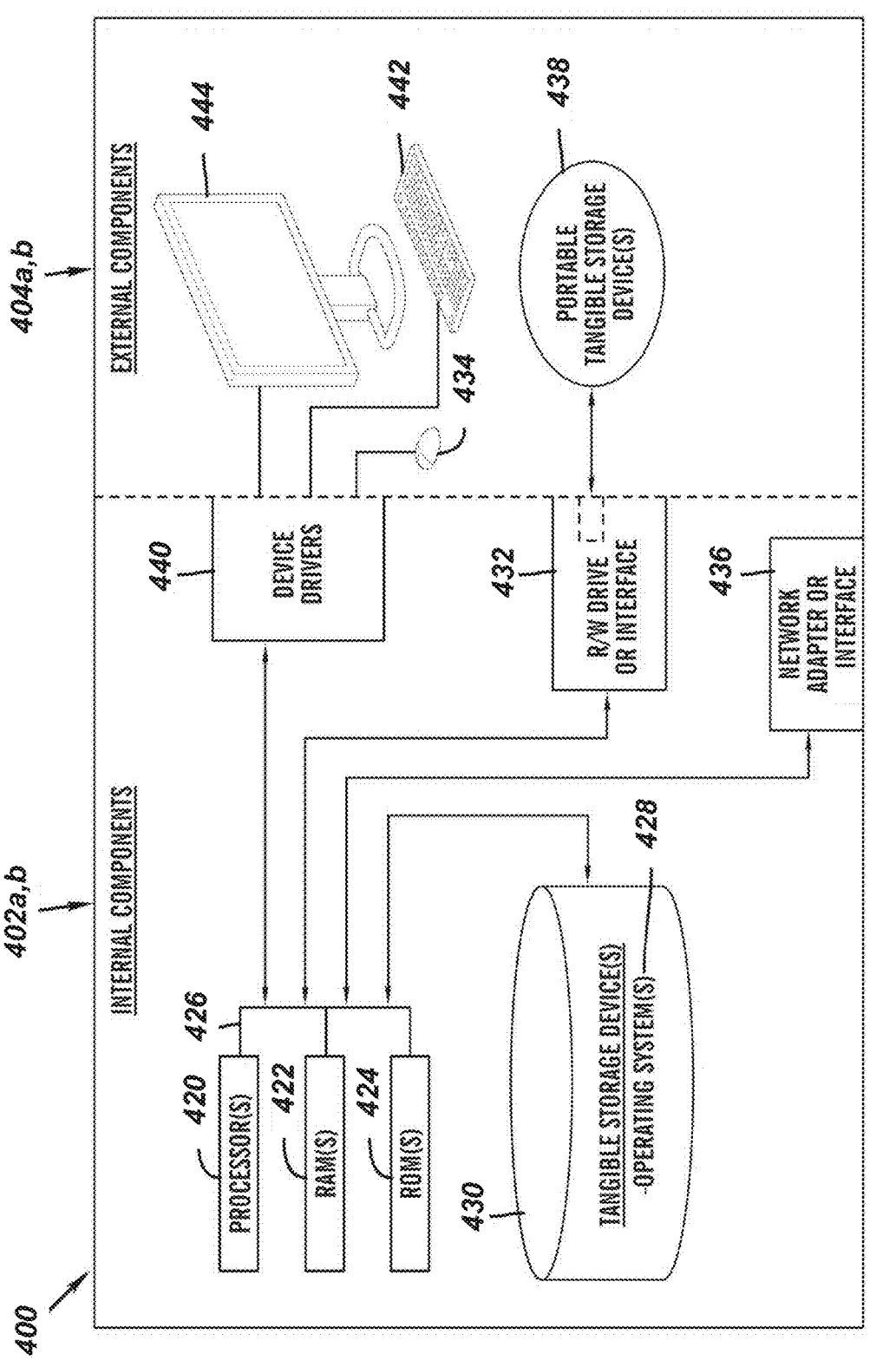
FIG. 4 is a functional block diagram of internal and external components of computers and servers depicted in FIG. 1 according to at least one embodiment.

FIG. 4 is a block diagram 400 of internal and external components of the client computing device 102 and the server 112 depicted in FIG. 1 in accordance with an embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

The data processing system 402, 404 is representative of any electronic device capable of executing machine-readable program instructions. The data processing system 402, 404 may be representative of a smart phone, a computer system, PDA, or other electronic devices. Examples of computing systems, environments, and/or configurations that may represented by the data processing system 402, 404 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

The client computing device 102 and the server 112 may include respective sets of internal components 402 *a,b* and external components 404 *a,b* illustrated in FIG. 4. Each of the sets of internal components 402 include one or more processors 420, one or more computer-readable RAMs 422, and one or more computer-readable ROMs 424 on one or more buses 426, and one or more operating systems 428 and one or more computer-readable tangible storage devices 430. The one or more operating systems 428, the software program 108 and the vehicle decontamination program 110A in the client computing device 102 and the vehicle decontamination program 110B in the server 112 are stored on one or more of the respective computer-readable tangible storage devices 430 for execution by one or more of the respective processors 420 via one or more of the respective RAMs 422 (which typically include cache memory). In the embodiment illustrated in FIG. 4, each of the computer-readable tangible storage devices 430 is a magnetic disk storage device of an internal hard drive. Alternatively, each of the computer-readable tangible storage devices 430 is a semiconductor storage device such as ROM 424, EPROM, flash memory or any other computer-readable tangible storage device that can store a computer program and digital information.

Each set of internal components 402 *a,b* also includes a R/W drive or interface 432 to read from and write to one or more portable computer-readable tangible storage devices 438 such as a CD-ROM, DVD, memory stick, magnetic tape, magnetic disk, optical disk or semiconductor storage device. A software program, such as the vehicle decontamination program 110A, 110B, can be stored on one or more of the respective portable computer-readable tangible storage devices 438, read via the respective RAY drive or interface 432, and loaded into the respective hard drive 430.

Each set of internal components 402 *a,b* also includes network adapters or interfaces 436 such as a TCP/IP adapter cards, wireless Wi-Fi interface cards, or 3G or 4G wireless interface cards or other wired or wireless communication links. The software program 108 and the vehicle decontamination program 110A in the client computing device 102 and the vehicle decontamination program 110B in the server 112 can be downloaded to the client computing device 102 and the server 112 from an external computer via a network (for example, the Internet, a local area network or other, wide area network) and respective network adapters or interfaces 436. From the network adapters or interfaces 436, the software program 108 and the vehicle decontamination program 110A in the client computing device 102 and the vehicle decontamination program 110B in the server 112 are loaded into the respective hard drive 430. The network may comprise copper wires, optical fibers, wireless transmission, routers, firewalls, switches, gateway computers and/or edge servers.

Each of the sets of external components 404 *a,b* can include a computer display monitor 444, a keyboard 442, and a computer mouse 434. External components 404 *a,b* can also include touch screens, virtual keyboards, touch pads, pointing devices, and other human interface devices. Each of the sets of internal components 402 *a,b* also includes device drivers 440 to interface to computer display monitor 444, keyboard 442, and computer mouse 434. The device drivers 440, R/W drive or interface 432, and network adapter or interface 436 comprise hardware and software (stored in storage device 430 and/or ROM 424).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
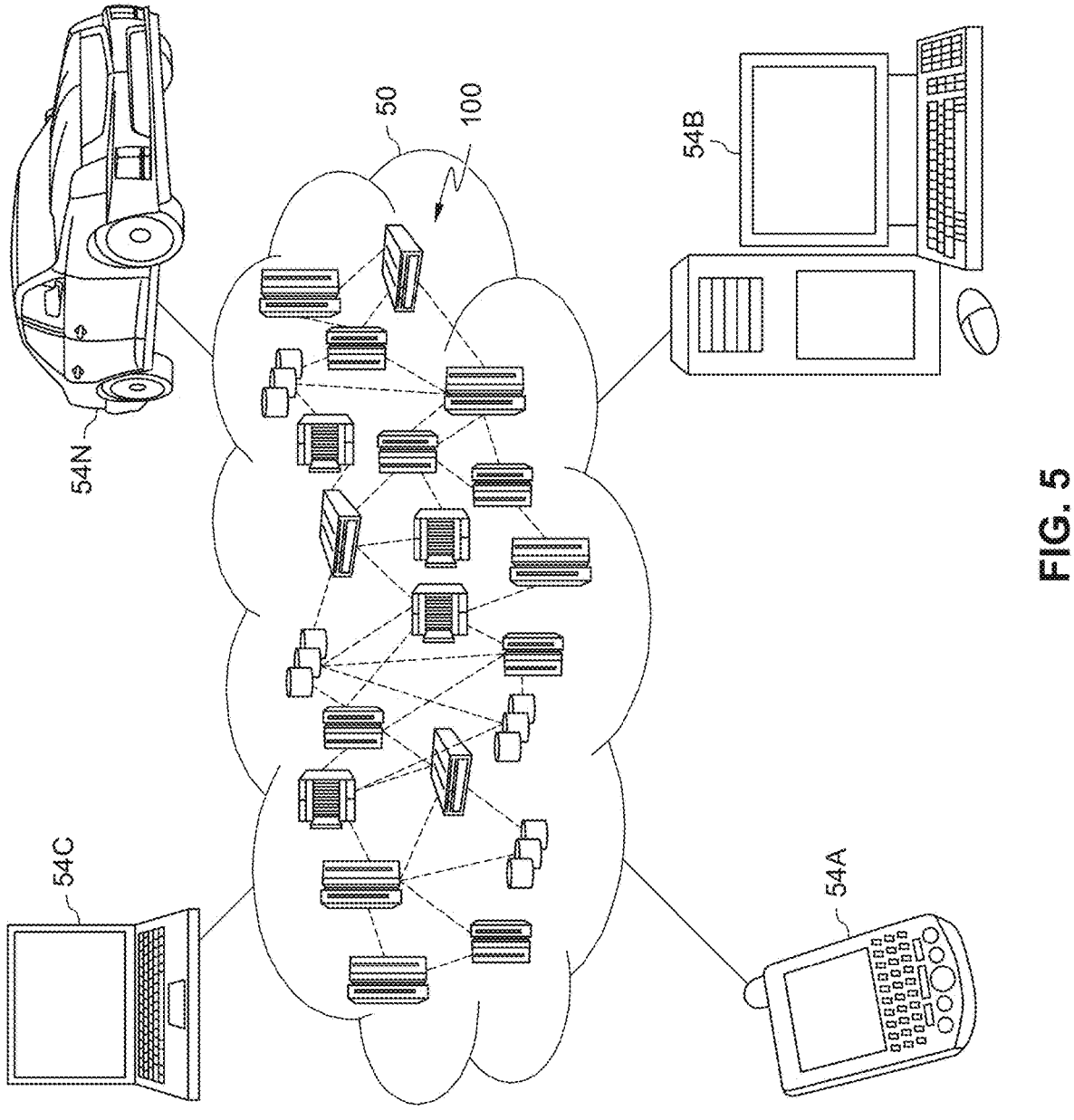
FIG. 5 depicts a cloud computing environment according to an embodiment of the present invention.

Referring now to FIG. 5, illustrative cloud computing environment 50 is depicted. As shown, cloud computing environment 50 comprises one or more cloud computing nodes 100 with which local computing devices used by cloud consumers, such as, for example, personal digital assistant (PDA) or cellular telephone 54A, desktop computer 54B, laptop computer 54C, and/or automobile computer system 54N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 100 and cloud computing environment 50 can communicate with any type of computerized device over any type of network and/or network addressable connection (e.g., using a web browser).

Figure 6:
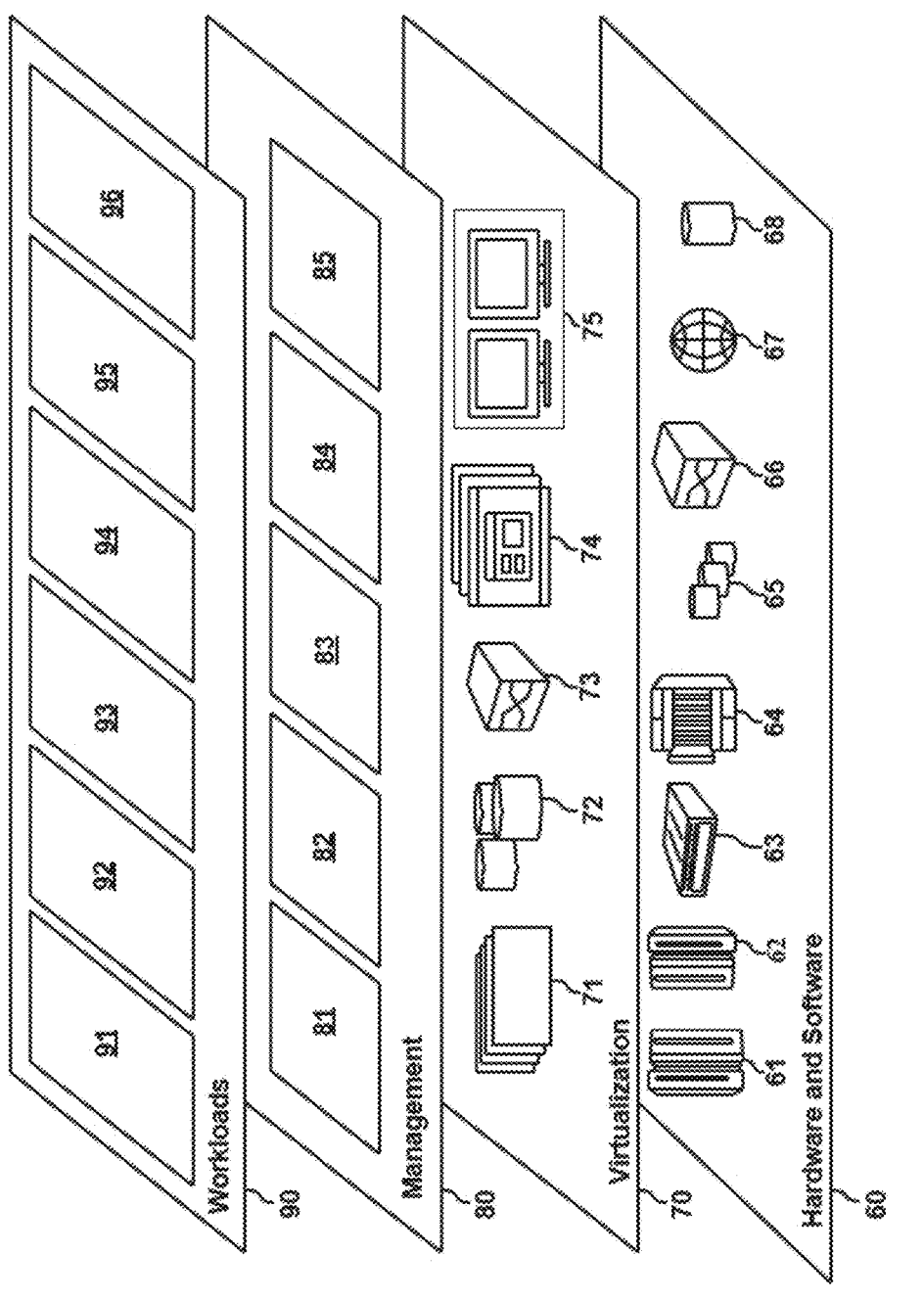
FIG. 6 depicts abstraction model layers according to an embodiment of the present invention.

Referring now to FIG. 6, a set of functional abstraction layers 600 provided by cloud computing environment 50 is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and decontaminating transportation vehicles 96. Decontaminating transportation vehicles 96 may relate to predicting one or more target areas of a transportation vehicle to decontaminate based on a route and historical data in order to deploy one or more decontamination devices to sanitize one or more parts of the transportation vehicle.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-based method of decontaminating transportation vehicles, the method comprising:
   receiving GPS data and real-time and historical data relating to contamination for a transportation vehicle from one or more sources in a surrounding environment;

identifying a route and a location of the transportation vehicle based on the GPS data;
   predicting one or more target areas of the transportation vehicle to decontaminate based on the route and the historical data, wherein the predicted one or more target areas include one or more pre-determined locations on the transportation vehicle most likely to become contaminated along a current route based on prior instances of contamination of the transportation vehicle on the current route contained in the historical data;
   placing one or more decontamination devices at the predicted one or more target areas;
   identifying one or more parts of the transportation vehicle requiring decontamination based on the real-time data from the one or more sources and the location of the transportation vehicle;
   determining whether at least one type of contamination is airborne;
   in response to determining the at least one type of contamination is airborne:
      activating the one or more decontamination devices to increase air pressure inside a portion of the transportation vehicle based on a type of the transportation vehicle; and
      releasing the air pressure inside the portion of the transportation vehicle when a door is opened; and
   deploying the one or more decontamination devices to sanitize the one or more parts of the transportation vehicle requiring decontamination.

2. The computer-based method of claim 1, further comprising:
   determining whether an external object is interacting with the transportation vehicle; and
   in response to determining the external object is interacting with the transportation vehicle, deploying the one or more decontamination devices to sanitize the external object.

3. The computer-based method of claim 2, wherein the external object is prevented from entering an interior of the transportation vehicle while the deployed one or more decontamination devices sanitize the external object.

4. The computer-based method of claim 1, wherein the one or more decontamination devices include a plurality of blowers, and the air pressure inside the portion of the transportation vehicle is released by blowing air out of the portion of the transportation vehicle when the door is opened.

5. The computer-based method of claim 1, wherein the one or more decontamination devices include a plurality of drones, and deploying the one or more decontamination devices to sanitize the one or more parts of the transportation vehicle requiring decontamination further comprises:
   detaching the plurality of drones from a surface of the transportation vehicle while the transportation vehicle is in motion, wherein the detached plurality of drones synchronously move relative to the transportation vehicle to sanitize the one or more parts.

6. The computer-based method of claim 5, wherein the detached plurality of drones sanitize the one or more parts by spraying a chemical on the one or more parts while the transportation vehicle is in motion.

7. The computer-based method of claim 1, wherein the source is selected from a group consisting of a plurality of odor detection sensors, a GPS device, and a database containing information about air quality in a geographical area.

8. A computer system, the computer system comprising:
one or more processors, one or more computer-readable memories, one or more computer-readable tangible storage medium, and program instructions stored on at least one of the one or more computer-readable tangible storage medium for execution by at least one of the one or more processors via at least one of the one or more computer-readable memories, wherein the computer system is capable of performing a method comprising:
receiving GPS data and real-time and historical data relating to contamination for a transportation vehicle from one or more sources in a surrounding environment;
identifying a route and a location of the transportation vehicle based on the GPS data;
predicting one or more target areas of the transportation vehicle to decontaminate based on the route and the historical data, wherein the predicted one or more target areas include one or more pre-determined locations on the transportation vehicle most likely to become contaminated along a current route based on prior instances of contamination of the transportation vehicle on the current route contained in the historical data;
placing one or more decontamination devices at the predicted one or more target areas;
identifying one or more parts of the transportation vehicle requiring decontamination based on the real-time data from the one or more sources and the location of the transportation vehicle;
determining whether at least one type of contamination is airborne;
in response to determining the at least one type of contamination is airborne:
activating the one or more decontamination devices to increase air pressure inside a portion of the transportation vehicle based on a type of the transportation vehicle; and
releasing the air pressure inside the portion of the transportation vehicle when a door is opened; and
deploying the one or more decontamination devices to sanitize the one or more parts of the transportation vehicle requiring decontamination.

9. The computer system of claim 8, further comprising:
determining whether an external object is interacting with the transportation vehicle; and
in response to determining the external object is interacting with the transportation vehicle, deploying the one or more decontamination devices to sanitize the external object.

10. The computer system of claim 9, wherein the external object is prevented from entering an interior of the transportation vehicle while the deployed one or more decontamination devices sanitize the external object.

11. The computer system of claim 8, wherein the one or more decontamination devices include a plurality of blowers, and the air pressure inside the portion of the transportation vehicle is released by blowing air out of the portion of the transportation vehicle when the door is opened.

12. The computer system of claim 8, wherein the one or more decontamination devices include a plurality of drones, and deploying the one or more decontamination devices to sanitize the one or more parts of the transportation vehicle requiring decontamination further comprises:
detaching the plurality of drones from a surface of the transportation vehicle while the transportation vehicle is in motion, wherein the detached plurality of drones synchronously move relative to the transportation vehicle to sanitize the one or more parts.

13. The computer system of claim 12, wherein the detached plurality of drones sanitize the one or more parts by spraying a chemical on the one or more parts while the transportation vehicle is in motion.

14. The computer system of claim 8, wherein the source is selected from a group consisting of a plurality of odor detection sensors, a GPS device, and a database containing information about air quality in a geographical area.

15. A computer program product, the computer program product comprising:
one or more computer-readable tangible storage medium and program instructions stored on at least one of the one or more computer-readable tangible storage medium, the program instructions executable by a processor capable of performing a method, the method comprising:
receiving GPS data and real-time and historical data relating to contamination for a transportation vehicle from one or more sources in a surrounding environment;
identifying a route and a location of the transportation vehicle based on the GPS data;
predicting one or more target areas of the transportation vehicle to decontaminate based on the route and the historical data, wherein the predicted one or more target areas include one or more pre-determined locations on the transportation vehicle most likely to become contaminated along a current route based on prior instances of contamination of the transportation vehicle on the current route contained in the historical data;
placing one or more decontamination devices at the predicted one or more target areas;
identifying one or more parts of the transportation vehicle requiring decontamination based on the real-time data from the one or more sources and the location of the transportation vehicle;
determining whether at least one type of contamination is airborne;
in response to determining the at least one type of contamination is airborne:
activating the one or more decontamination devices to increase air pressure inside a portion of the transportation vehicle based on a type of the transportation vehicle; and
releasing the air pressure inside the portion of the transportation vehicle when a door is opened; and
deploying the one or more decontamination devices to sanitize the one or more parts of the transportation vehicle requiring decontamination.

16. The computer program product of claim 15, further comprising:
determining whether an external object is interacting with the transportation vehicle; and
in response to determining the external object is interacting with the transportation vehicle, deploying the one or more decontamination devices to sanitize the external object.

17. The computer program product of claim 16, wherein the external object is prevented from entering an interior of the transportation vehicle while the deployed one or more decontamination devices sanitize the external object.

18. The computer program product of claim 15, wherein the one or more decontamination devices include a plurality of blowers, and the air pressure inside the portion of the transportation vehicle is released by blowing air out of the portion of the transportation vehicle when the door is opened.

19. The computer program product of claim 15, wherein the one or more decontamination devices include a plurality of drones, and deploying the one or more decontamination devices to sanitize the one or more parts of the transportation vehicle requiring decontamination further comprises:

detaching the plurality of drones from a surface of the transportation vehicle while the transportation vehicle is in motion, wherein the detached plurality of drones synchronously move relative to the transportation vehicle to sanitize the one or more parts.

20. The computer program product of claim 19, wherein the detached plurality of drones sanitize the one or more parts by spraying a chemical on the one or more parts while the transportation vehicle is in motion.

\*   \*   \*   \*   \*